(12) United States Patent
Hines et al.

(10) Patent No.: US 10,065,036 B2
(45) Date of Patent: *Sep. 4, 2018

(54) METHOD FOR MEASURING STABLE AND REPRODUCIBLE ELECTRODE-TISSUE IMPEDANCE

(75) Inventors: Amy Chu Peishuan Hines, Monterey Park, CA (US); Dao Min Zhou, Saugus, CA (US); Arup Roy, Valencia, CA (US); Rongqing Dai, Valencia, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 1278 days.

This patent is subject to a terminal disclaimer.

(21) Appl. No.: 11/906,167

(22) Filed: Sep. 28, 2007

(65) Prior Publication Data

US 2008/0082140 A1 Apr. 3, 2008

Related U.S. Application Data

(60) Provisional application No. 60/848,305, filed on Sep. 29, 2006.

(51) Int. Cl.
*A61N 1/36* (2006.01)
*A61N 1/05* (2006.01)

(52) U.S. Cl.
CPC ....... *A61N 1/36046* (2013.01); *A61N 1/0543* (2013.01)

(58) Field of Classification Search
CPC .............. A61N 1/36046; A61N 1/0543
USPC ................................... 607/28, 53, 54
See application file for complete search history.

(56) References Cited

U.S. PATENT DOCUMENTS

| | | | |
|---|---|---|---|
| 4,573,481 A | 3/1986 | Bullara | |
| 4,577,640 A * | 3/1986 | Hofmeister | 600/551 |
| 4,628,933 A | 12/1986 | Michelson | |
| 4,837,049 A | 6/1989 | Byers et al. | |
| 5,109,844 A | 5/1992 | de Juan, Jr. et al. | |
| 5,172,690 A * | 12/1992 | Nappholz et al. | 607/13 |
| 5,201,865 A * | 4/1993 | Kuehn | A61N 1/3706 607/28 |
| 5,215,088 A | 6/1993 | Normann et al. | |
| 5,507,785 A * | 4/1996 | Deno | 607/24 |
| 5,935,155 A * | 8/1999 | Humayun et al. | 607/54 |
| 6,400,989 B1 | 6/2002 | Eckmiller | |

(Continued)

OTHER PUBLICATIONS

Weiland et al., "Chronic Neural Stimulation with Thin-Film, Iridium Oxide Electrodes," IEEE Transactions on Biomedical Engineering, vol. 47, No. 7, Jul. 2000.*

(Continued)

*Primary Examiner* — Eric D. Bertram
(74) *Attorney, Agent, or Firm* — Scott Dunbar

(57) ABSTRACT

The present invention is a method for measuring stable and reproducible electrode-tissue impedance, comprising preconditioning an electrode-tissue interface. Further aspect of the invention is a stimulation system for a visual prosthesis generating a stimulation signal to precondition the electrode-tissue interface, comprising a computer; software, loaded in the computer, adapted to perform a stimulating method for a visual prosthesis having a plurality of electrodes; a video processing unit; and an implanted neuron-stimulator.

8 Claims, 4 Drawing Sheets

(56) References Cited

U.S. PATENT DOCUMENTS

| | | |
|---|---|---|
| 6,458,157 B1 | 10/2002 | Suaning |
| 6,974,533 B2 | 12/2005 | Zhou |
| 7,181,287 B2 | 2/2007 | Greenberg |
| 2002/0091422 A1* | 7/2002 | Greenberg et al. ............ 607/54 |
| 2002/0111658 A1 | 8/2002 | Greenberg et al. |
| 2003/0139784 A1 | 7/2003 | Morimoto et al. |
| 2003/0195601 A1 | 10/2003 | Hung et al. |
| 2004/0215275 A1* | 10/2004 | Vonk et al. .................... 607/28 |
| 2004/0220652 A1 | 11/2004 | Zhou et al. |
| 2005/0043766 A1* | 2/2005 | Soykan ............... A61L 27/3839 607/9 |
| 2005/0131490 A1 | 6/2005 | Palanker |
| 2005/0271895 A1 | 12/2005 | Zhou |
| 2006/0063062 A1 | 3/2006 | Zhou et al. |
| 2006/0129207 A1 | 6/2006 | Fried et al. |
| 2006/0247754 A1 | 11/2006 | Greenberg et al. |
| 2006/0259108 A1 | 11/2006 | Hung et al. |
| 2006/0259109 A1 | 11/2006 | Zhou et al. |
| 2006/0259112 A1 | 11/2006 | Greenberg et al. |
| 2007/0026048 A1 | 2/2007 | Greenberg |
| 2007/0089992 A1 | 4/2007 | Zhou |
| 2007/0089994 A1 | 4/2007 | Zhou |
| 2007/0092750 A1 | 4/2007 | Zhou |
| 2007/0092786 A1 | 4/2007 | Zhou |
| 2007/0173905 A1 | 7/2007 | Greenberg et al. |
| 2007/0191911 A1 | 8/2007 | Greenberg et al. |
| 2007/0265665 A1 | 11/2007 | Greenberg et al. |
| 2009/0292346 A1* | 11/2009 | Norlin ................... A61N 1/05 607/119 |

OTHER PUBLICATIONS

Eugene De Juan, Retinal Tacks, American Journal of Ophthalmology 99: pp. 272-274, Mar. 1985.

* cited by examiner

METHOD FOR MEASURING STABLE AND REPRODUCIBLE ELECTRODE-TISSUE IMPEDANCE

CROSS-REFERENCE TO RELATED APPLICATIONS

This application claims benefit of U.S. Provisional Patent application Ser. No. 60/848,305, filed on Sep. 29, 2006, entitled "Method for measuring stable and reproducible electrode-tissue impedance," the disclosure of which is incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to a method for measuring stable and reproducible electrode-tissue impedance

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

In-vivo electrode-tissue impedance measurements in prostheses suffer from high variation, poor reproducibility. The present invention is a Pre-conditioning the electrode-tissue interface is helpful in achieving reproducibility and reliability of electrode-tissue impedance measurement data. The impedance measurements can also be used to accurately study correlation with measurements of distance of the electrode array from the sensory surface, and correlation with perceptual thresholds and compliance voltage limits. Further aspect of the invention is a stimulation system for a visual prosthesis generating a stimulation signal to precondition the electrode-tissue interface, comprising a computer; software, loaded in the computer, adapted to perform a stimulating method for a visual prosthesis having a plurality of electrodes; a video processing unit; and an implanted neuron-stimulator.

DETAILED DESCRIPTION OF THE PREFERRED EMBODIMENTS

Figure 1:
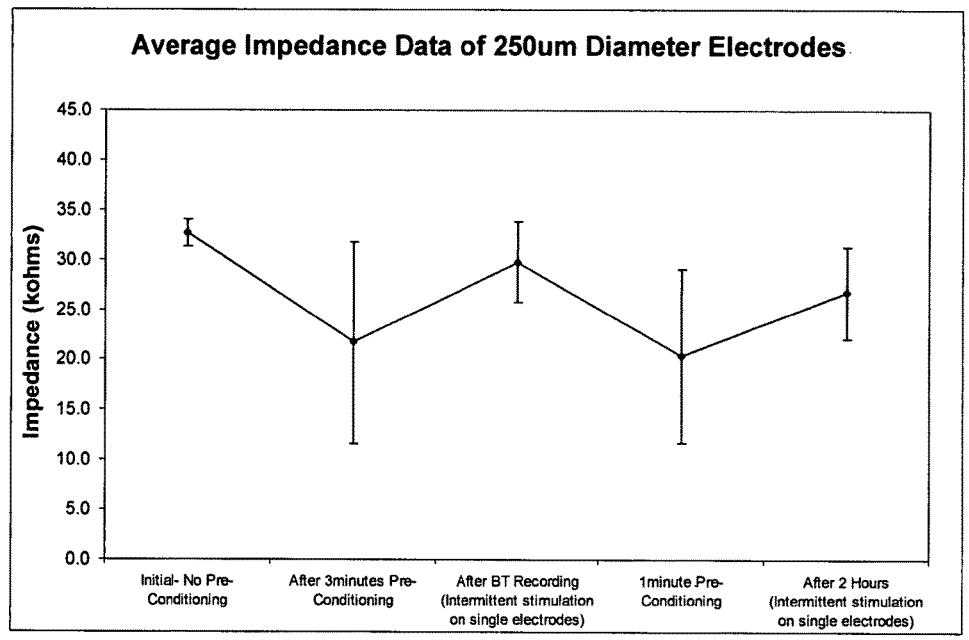
FIG. 1 shows a chart of average impedance data for 250 μm D electrodes.

The present invention is an improved method for measuring stable and reproducible electrode-tissue impedance. The method comprises the preconditioning of an electrode-tissue interface. In-vivo electrode-tissue impedance measurements in prostheses show great variations, depending on the stimulation history on the electrodes. The variations are significant especially for micro-electrodes in an electrode array.

Any changes in impedance values can be observed when the stimulation is turned off for a period of a time, for example overnight. This is due to the variation in the electrode/tissue interface. The interface can be protein absorption and/or ion absorption on the electrode surface. The variations alter the electrode/electrolyte interface. This causes a variation of the electrode impedance.

Although, a double layer capacitance is much more sensitive to such change, both resistance and capacitance are altered by the interface change. It has been surprisingly shown that preconditioning of the electrode-tissue interface can be achieved by simulating the electrodes with a small stimulation current or voltage for a certain period of time.

The stimulation current amplitude is chosen to cause non-faradaic reactions in the electrode-tissue interface. Such reactions reduce the absorptions and diffusion layer thickness. Therefore a uniform electrode-tissue interface is reached quickly.

The measurements are performed at similar electrode-tissue interface conditions, thus variations for each electrode on an array are reduced. For example in a 16 electrode array, a three minute preconditioning stimulation with a biphasic, charge balanced square wave pulse current (Tx=Ty=Tx=0.3 ms, current=10 μA, 50 Hz) reduces the standard deviation of electrode-tissue impedance from 4.8 to 2.3 for the individual electrodes and from 7.44 to 4.06 for the whole array. Further, the measurement results were much more reproducible with pre-conditioning than without.

In the context of the present disclosure Back Telemetry stands for Back Telemetry Voltage Waveform, which is the information received back from an implant via a RF link. Voltage waveform Rs is the resistance of the electrode material and electrolyte calculated by taking the measured incidental voltage change at the start of current stimulation divided by the current used (Ohm's Law: Resistance=Voltage/Current). The waveform is obtained through back telemetry of the electronics, hence labeled Back Telemetry Rs. These measurements are shown and explained in the following tables 1-5 for patients A, B, and C.

In the context of the present disclosure PCIT stands for Portable Cochlear Implant Tester. PCIT is a device (from the Advanced Bionics Corporation) that provides quick impedance measurements of the electrodes. These measurements are shown and explained in the following tables 6-12 for patients A, B, and C.

TABLE 1

| Patient A | | | |
|---|---|---|---|
| 250 μm D | | Back Telemetry Rs | |
| Electrode | | Measurement 1 | Measurement 2 |
| M1 | 1 | 8.2 | 8.7 |
| L1 | 2 | 9.9 | 9.6 |
| M2 | 3 | 9.4 | 8.9 |
| L2 | 4 | 8.5 | 8.8 |
| M3 | 5 | 10.4 | 10.0 |
| L3 | 6 | 8.7 | 8.8 |
| M4 | 7 | 8.5 | 7.6 |
| L4 | 8 | 8.9 | 8.8 |
| M5 | 9 | 10.4 | 10.1 |
| L5 | 10 | 8.7 | 8.6 |
| M6 | 11 | 9.9 | 9.6 |
| L6 | 12 | 9.6 | 9.6 |
| M7 | 13 | 10.1 | 10.4 |
| L7 | 14 | 9.0 | 9.0 |
| M8 | 15 | 8.9 | 8.6 |
| L8 | 16 | 10.6 | 10.7 |
| | Average | 9.4 | 9.2 |
| | St. dev. | 0.78 | 0.81 |

TABLE 2

| Patient B | | | | |
|---|---|---|---|---|
| 250 μm D | | Back Telemetry Rs | | |
| Electrode | | Measurement 1 | Measurement 2 | Measurement 3 |
| M1 | 1 | 11.3 | 11.1 | 12.0 |
| L1 | 2 | 9.0 | 9.5 | 12.1 |
| M3 | 5 | 11.2 | 11.5 | 11.4 |
| L3 | 6 | 11.2 | 11.3 | 11.7 |
| M6 | 11 | 13.9 | 13.3 | 13.5 |

TABLE 2-continued

Patient B

250 μm D — Back Telemetry Rs

| Electrode | | Measurement 1 | Measurement 2 | Measurement 3 |
|---|---|---|---|---|
| L6 | 12 | 10.5 | 10.2 | 10.6 |
| M8 | 15 | 11.2 | 12.3 | 11.8 |
| L8 | 16 | 11.1 | 10.8 | 11.9 |
| Average | | 11.2 | 11.3 | 11.9 |
| St. dev. | | 1.34 | 1.17 | 0.80 |

TABLE 3

Patient B

500 μm D — Back Telemetry Rs

| Electrode | | Measurement 1 | Measurement 2 | Measurement 3 |
|---|---|---|---|---|
| M2 | 3 | 9.4 | 9.2 | 9.5 |
| L2 | 4 | 7.4 | 8.0 | 7.9 |
| M4 | 7 | 8.8 | 8.5 | 8.9 |
| L4 | 8 | 8.1 | 8.0 | 8.6 |
| M5 | 9 | 9.5 | 9.6 | 9.9 |
| L5 | 10 | 8.2 | 8.0 | 8.3 |
| M7 | 13 | 8.8 | 9.3 | 9.0 |
| L7 | 14 | 8.1 | 8.3 | 8.6 |
| Average | | 8.5 | 8.6 | 8.8 |
| St. dev. | | 0.73 | 0.67 | 0.65 |

TABLE 4

Patient C

250 μm D — Back Telemetry Rs

| Electrode | | Measurement 1 | Measurement 2 |
|---|---|---|---|
| M1 | 1 | 11.9 | 10.8 |
| L1 | 2 | 10.4 | 10.0 |
| M3 | 5 | 11.1 | 10.4 |
| L3 | 6 | 10.4 | 9.9 |
| M6 | 11 | 11.2 | 10.4 |
| L6 | 12 | 10.1 | 11.8 |
| M8 | 15 | 10.6 | 9.8 |
| L8 | 16 | 12.9 | 12.9 |
| Average | | 11.1 | 10.7 |
| St. dev. | | 0.93 | 1.08 |

TABLE 5

Patient C

500 μm D — Back Telemetry Rs

| Electrode | | Measurement 1 | Measurement 2 |
|---|---|---|---|
| M2 | 3 | 8.3 | 8.1 |
| L2 | 4 | 7.4 | 7.0 |
| M4 | 7 | 7.7 | 7.6 |
| L4 | 8 | 7.6 | 7.3 |
| M5 | 9 | 8.2 | 8.1 |
| L5 | 10 | 8.2 | 6.8 |
| M7 | 13 | 8.8 | 8.5 |
| L7 | 14 | 6.8 | 6.8 |
| Average | | 7.9 | 7.5 |
| St. dev. | | 0.64 | 0.65 |

TABLE 6

Patient A

250 μm D — PCIT Initial

| Electrode | | Measurement 1 | Measurement 2 |
|---|---|---|---|
| M1 | 1 | 21.8 | 28.6 |
| L1 | 2 | 24 | 26.5 |
| M2 | 3 | 23.3 | 29.3 |
| L2 | 4 | 23.5 | 23.9 |
| M3 | 5 | 30.3 | 31.9 |
| L3 | 6 | 25.8 | 26.3 |
| M4 | 7 | 17.2 | 12.1 |
| L4 | 8 | 29.4 | 24.3 |
| M5 | 9 | 38.2 | 31.5 |
| L5 | 10 | 31.5 | 25 |
| M6 | 11 | 33.1 | 35.1 |
| L6 | 12 | 31 | 30.4 |
| M7 | 13 | 34.4 | 36.2 |
| L7 | 14 | 35.9 | 29.5 |
| M8 | 15 | 27.8 | 22.3 |
| L8 | 16 | 43.9 | 46.8 |
| Average | | 29.4 | 28.7 |
| St. dev. | | 6.83 | 7.44 |

TABLE 7

Patient B

250 μm D — PCIT Initial

| Electrode | | Measurement 1 | Measurement 2 | Measurement 3 |
|---|---|---|---|---|
| M1 | 1 | 33.6 | 31.5 | 33.2 |
| L1 | 2 | 20.0 | 32.5 | 33.1 |
| M3 | 5 | 31.5 | 30.7 | 27.2 |
| L3 | 6 | 33.2 | 30.9 | 27.6 |
| M6 | 11 | 49.5 | 40.2 | 47.7 |
| L6 | 12 | 26.7 | 25.5 | 20.9 |
| M8 | 15 | 43.5 | 36.4 | 46.3 |
| L8 | 16 | 40.5 | 38.7 | 52.1 |
| Average | | 34.8 | 33.3 | 36.0 |
| St. dev. | | 9.44 | 4.83 | 11.30 |

TABLE 8

Patient B

500 μm D — PCIT Initial

| Electrode | | Measurement 1 | Measurement 2 | Measurement 3 |
|---|---|---|---|---|
| M2 | 3 | 18.6 | 17.3 | 17.9 |
| L2 | 4 | 15.3 | 24.1 | 20.9 |
| M4 | 7 | 21.1 | 20.1 | 19.6 |
| L4 | 8 | 16.7 | 17.3 | 17.9 |
| M5 | 9 | 19.8 | 19.8 | 18.5 |
| L5 | 10 | 20.3 | 16.1 | 16.0 |
| M7 | 13 | 21.4 | 21.1 | 24.0 |
| L7 | 14 | 18.8 | 19.0 | 22.0 |
| Average | | 19.0 | 19.4 | 19.6 |
| St. dev. | | 2.13 | 2.55 | 2.59 |

TABLE 9

Patient C

250 μm D — PCIT Initial

| Electrode | | Measurement 1 | Measurement 2 |
|---|---|---|---|
| M1 | 1 | 26.9 | 30.5 |
| L1 | 2 | 31.2 | 30.8 |

TABLE 9-continued

Patient C

| | 250 μm D | PCIT Initial | |
|---|---|---|---|
| Electrode | | Measurement 1 | Measurement 2 |
| M3 | 5 | 27.1 | 28.3 |
| L3 | 6 | 27.1 | 28.6 |
| M6 | 11 | 35.1 | 38.4 |
| L6 | 12 | 35.7 | 36.7 |
| M8 | 15 | 32.0 | 35.1 |
| L8 | 16 | 70.1 | 75.7 |
| | Average | 35.7 | 38.0 |
| | St. dev. | 14.36 | 15.68 |

TABLE 10

Patient C

| | 500 μm D | PCIT Initial | |
|---|---|---|---|
| Electrode | | Measurement 1 | Measurement 2 |
| M2 | 3 | 15.9 | 15.0 |
| L2 | 4 | 16.0 | 15.6 |
| M4 | 7 | 17.3 | 17.1 |
| L4 | 8 | 22.0 | 22.3 |
| M5 | 9 | 18.1 | 19.9 |
| L5 | 10 | 17.7 | 18.1 |
| M7 | 13 | 24.7 | 22.3 |
| L7 | 14 | 17.0 | 16.6 |
| | Average | 18.6 | 18.4 |
| | St. dev. | 3.12 | 2.86 |

TABLE 11

Patient A

| | 250 μm D | After 3 min Conditioning | |
|---|---|---|---|
| Electrode | | Measurement 1 | Measurement 2 |
| M1 | 1 | 17.7 | 20.9 |
| L1 | 2 | 30.2 | 29.3 |
| M2 | 3 | 25.1 | 25.5 |
| L2 | 4 | 15.9 | 16.5 |
| M3 | 5 | 21.4 | 22.2 |
| L3 | 6 | 19.9 | 19.6 |
| M4 | 7 | 15.7 | 13.2 |
| L4 | 8 | 18.7 | 17.9 |
| M5 | 9 | 23.6 | 24.6 |
| L5 | 10 | 18.4 | 21.2 |
| M6 | 11 | 23.1 | 22.0 |
| L6 | 12 | 18.4 | 19.3 |
| M7 | 13 | 22.1 | 21.7 |
| L7 | 14 | 21.5 | 17.6 |
| M8 | 15 | 17.2 | 15.9 |
| L8 | 16 | 23.7 | 24.1 |
| | Average | 20.8 | 20.7 |
| | St. dev. | 3.83 | 4.06 |

TABLE 12

Patient B

| | 250 μm D | After 3 min Conditioning | | |
|---|---|---|---|---|
| Electrode | | Measurement 1 | Measurement 2 | Measurement 3 |
| M1 | 1 | 24.7 | 25.0 | 26.4 |
| L1 | 2 | 15.9 | 23.4 | 22.5 |
| M3 | 5 | 24.4 | 25.9 | 26.0 |
| L3 | 6 | 24.0 | 29.2 | 25.2 |

TABLE 12-continued

Patient B

| | 250 μm D | After 3 min Conditioning | | |
|---|---|---|---|---|
| Electrode | | Measurement 1 | Measurement 2 | Measurement 3 |
| M6 | 11 | 29.7 | 28.9 | 25.1 |
| L6 | 12 | 20.7 | 19.4 | 20.1 |
| M8 | 15 | 21.5 | 24.0 | 24.1 |
| L8 | 16 | 22.0 | 20.2 | 25.0 |
| | Average | 22.9 | 24.5 | 24.3 |
| | St. dev. | 3.96 | 3.58 | 2.08 |

TABLE 13

Patient B

| | 500 μm D | After 3 min Conditioning | | |
|---|---|---|---|---|
| Electrode | | Measurement 1 | Measurement 2 | Measurement 3 |
| M2 | 3 | 18.6 | 19.7 | 19.3 |
| L2 | 4 | 13.8 | 17.7 | 16.8 |
| M4 | 7 | 16.6 | 15.3 | 16.0 |
| L4 | 8 | 15.2 | 16.5 | 15.5 |
| M5 | 9 | 17.7 | 19.4 | 17.4 |
| L5 | 10 | 14.3 | 15.5 | 13.5 |
| M7 | 13 | 16.4 | 17.2 | 15.8 |
| L7 | 14 | 14.0 | 14.4 | 14.4 |
| | Average | 15.8 | 17.0 | 16.1 |
| | St. dev. | 1.78 | 1.92 | 1.79 |

TABLE 14

Patient C

| | 250 μm D | After 3 min Conditioning | |
|---|---|---|---|
| Electrode | | Measurement 1 | Measurement 2 |
| M1 | 1 | 25.5 | 19.0 |
| L1 | 2 | 21.4 | 17.9 |
| M3 | 5 | 16.4 | 17.5 |
| L3 | 6 | 15.9 | 15.5 |
| M6 | 11 | 20.1 | 18.6 |
| L6 | 12 | 19.6 | 21.6 |
| M8 | 15 | 20.0 | 17.8 |
| L8 | 16 | 30.7 | 27.8 |
| | Average | 21.2 | 19.5 |
| | St. dev. | 4.86 | 3.78 |

TABLE 15

Patient C

| | 500 μm D | After 3 min Conditioning | |
|---|---|---|---|
| Electrode | | Measurement 1 | Measurement 2 |
| M2 | 3 | 13.6 | 14.0 |
| L2 | 4 | 11.0 | 12.9 |
| M4 | 7 | 11.7 | 12.9 |
| L4 | 8 | 12.4 | 13.5 |
| M5 | 9 | 12.7 | 13.8 |
| L5 | 10 | 12.2 | 12.8 |
| M7 | 13 | 14.9 | 15.0 |
| L7 | 14 | 12.6 | 12.5 |
| | Average | 12.6 | 13.4 |
| | St. dev. | 1.19 | 0.82 |

TABLE 16

Patient A

| 250 μm D Electrode | | After BT Recording | |
|---|---|---|---|
| | | Measurement 1 No Conditioning | Measurement 2 1 min Conditioning |
| M1 | 1 | 43.8 | 20.8 |
| L1 | 2 | 37.1 | 21.1 |
| M2 | 3 | 23.8 | 17.7 |
| L2 | 4 | 19.8 | 17.1 |
| M3 | 5 | 30.9 | 22.9 |
| L3 | 6 | 26.4 | 15.3 |
| M4 | 7 | 13.1 | 11.6 |
| L4 | 8 | 34.9 | 20.9 |
| M5 | 9 | 43.4 | 24.4 |
| L5 | 10 | 17.0 | 15.1 |
| M6 | 11 | 20.1 | 18.7 |
| L6 | 12 | 32.4 | 19.4 |
| M7 | 13 | 41.4 | 24.2 |
| L7 | 14 | 15.7 | 15.1 |
| M8 | 15 | 13.6 | 12.3 |
| L8 | 16 | 29.9 | 22.7 |
| Average | | 27.7 | 18.7 |
| St. dev. | | 10.58 | 4.04 |

TABLE 17

Patient B

| 250 μm D Electrode | | After BT Recording | | |
|---|---|---|---|---|
| | | Measurement 1 No Conditioning | Measurement 2 No Conditioning | Measurement 3 1 min Conditioning |
| M1 | 1 | 37.9 | 36.4 | 23.3 |
| L1 | 2 | 19.9 | 35.9 | 20.9 |
| M3 | 5 | 32.0 | 24.4 | 24.8 |
| L3 | 6 | 33.6 | 31.0 | 24.2 |
| M6 | 11 | 38.2 | 35.1 | 24.1 |
| L6 | 12 | 27.3 | 24.5 | 19.4 |
| M8 | 15 | 39.7 | 34.3 | 23.9 |
| L8 | 16 | 40.4 | 24.3 | 16.3 |
| Average | | 33.6 | 30.7 | 22.1 |
| St. dev. | | 7.10 | 5.49 | 2.99 |

TABLE 18

Patient B

| 500 μm D Electrode | | After BT Recording | | |
|---|---|---|---|---|
| | | Measurement 1 No Conditioning | Measurement 2 No Conditioning | Measurement 3 1 min Conditioning |
| M2 | 3 | 22.5 | 21.3 | 18.1 |
| L2 | 4 | 15.3 | 26.8 | 14.9 |
| M4 | 7 | 23.1 | 19.0 | 15.4 |
| L4 | 8 | 17.7 | 17.8 | 14.2 |
| M5 | 9 | 19.2 | 21.6 | 15.7 |
| L5 | 10 | 17.0 | 18.3 | 13.7 |
| M7 | 13 | 21.7 | 21.4 | 15.2 |
| L7 | 14 | 18.1 | 19.8 | 14.2 |
| Average | | 19.3 | 20.8 | 15.2 |
| St. dev. | | 2.82 | 2.85 | 1.36 |

TABLE 19

Patient C

| 250 μm D Electrode | | After BT Recording | |
|---|---|---|---|
| | | Measurement 1 No Conditioning | Measurement 2 1 min Conditioning |
| M1 | 1 | 39.4 | 31.2 |
| L1 | 2 | 41.9 | 24.0 |
| M3 | 5 | 21.5 | 19.7 |
| L3 | 6 | 21.3 | 15.4 |
| M6 | 11 | 22.1 | 12.4 |
| L6 | 12 | 32.8 | 24.6 |
| M8 | 15 | 25.3 | 20.8 |
| L8 | 16 | 27.1 | 27.0 |
| Average | | 28.9 | 21.9 |
| St. dev. | | 8.19 | 6.13 |

TABLE 20

Patient C

| 500 μm D Electrode | | After BT Recording | |
|---|---|---|---|
| | | Measurement 1 No Conditioning | Measurement 2 1 min Conditioning |
| M2 | 3 | 15.7 | 16.4 |
| L2 | 4 | 15.5 | 15.1 |
| M4 | 7 | 18.1 | 17.3 |
| L4 | 8 | 24.1 | 12.3 |
| M5 | 9 | 20.3 | 16.7 |
| L5 | 10 | 11.2 | 8.5 |
| M7 | 13 | 19.9 | 16.2 |
| L7 | 14 | 11.8 | 10.1 |
| Average | | 17.1 | 14.1 |
| St. dev. | | 4.40 | 3.34 |

TABLE 21

Patient A

| 250 μm D Electrode | | Final (2 hrs after Back Telemetry) | |
|---|---|---|---|
| | | Measurement 1 | Measurement 2 |
| M1 | 1 | 17.9 | 24.7 |
| L1 | 2 | 19.8 | 23.4 |
| M2 | 3 | 17.2 | 20.1 |
| L2 | 4 | 11.0 | 14.8 |
| M3 | 5 | 25.5 | 21.0 |
| L3 | 6 | 22.2 | 17.8 |
| M4 | 7 | 10.8 | 11.0 |
| L4 | 8 | 22.7 | 17.3 |
| M5 | 9 | 32.3 | 23.0 |
| L5 | 10 | 12.8 | 14.1 |
| M6 | 11 | 18.6 | 19.0 |
| L6 | 12 | 23.2 | 17.2 |
| M7 | 13 | 33.0 | 25.3 |
| L7 | 14 | 13.1 | 14.4 |
| M8 | 15 | 12.2 | 11.2 |
| L8 | 16 | 23.2 | 18.1 |
| Average | | 19.7 | 18.3 |
| St. dev. | | 6.94 | 4.47 |

TABLE 22

Patient B

| 250 μm D Electrode | | Final (2 hrs after Back Telemetry) | |
|---|---|---|---|
| | | Measurement 1 | Measurement 2 |
| M1 | 1 | 40.7 | 42.2 |
| L1 | 2 | 19.9 | 41.0 |
| M3 | 5 | 36.4 | 39.3 |
| L3 | 6 | 34.2 | 40.6 |
| M6 | 11 | 40.2 | 39.8 |
| L6 | 12 | 28.5 | 29.1 |
| M8 | 15 | 40.9 | 35.9 |
| L8 | 16 | 40.4 | 30.0 |
| Average | | 35.2 | 37.2 |
| St. dev. | | 7.52 | 5.09 |

TABLE 23

Patient B

| 500 μm D Electrode | | Final (2 hrs after Back Telemetry) | |
|---|---|---|---|
| | | Measurement 1 | Measurement 2 |
| M2 | 3 | 26.2 | 24.7 |
| L2 | 4 | 17.6 | 16.6 |
| M4 | 7 | 22.9 | 22.5 |
| L4 | 8 | 17.4 | 14.0 |
| M5 | 9 | 22.2 | 23.9 |
| L5 | 10 | 19.4 | 18.4 |
| M7 | 13 | 21.3 | 21.8 |
| L7 | 14 | 18.6 | 19.6 |
| Average | | 20.7 | 20.2 |
| St. dev. | | 3.03 | 3.72 |

TABLE 24

Patient C

| 250 μm D Electrode | | Final (2 hrs after Back Telemetry) | |
|---|---|---|---|
| | | Measurement 1 | Measurement 2 |
| M1 | 1 | 43.1 | 30.2 |
| L1 | 2 | 45.8 | 31.0 |
| M3 | 5 | 28.6 | 23.9 |
| L3 | 6 | 28.9 | 21.2 |
| M6 | 11 | 29.7 | 20.9 |
| L6 | 12 | 32.3 | 29.9 |
| M8 | 15 | 28.2 | 32.1 |
| L8 | 16 | 48.6 | 50.1 |
| Average | | 35.7 | 29.9 |
| St. dev. | | 8.65 | 9.31 |

TABLE 25

Patient C

| 500 μm D Electrode | | Final (2 hrs after Back Telemetry) | |
|---|---|---|---|
| | | Measurement 1 | Measurement 2 |
| M2 | 3 | 16.1 | 15.7 |
| L2 | 4 | 19.4 | 16.0 |
| M4 | 7 | 19.4 | 10.2 |
| L4 | 8 | 23.8 | 15.3 |
| M5 | 9 | 21.7 | 18.2 |
| L5 | 10 | 13.0 | 10.5 |
| M7 | 13 | 20.7 | 17.7 |
| L7 | 14 | 15.1 | 13.0 |
| Average | | 18.7 | 14.6 |
| St. dev. | | 3.63 | 3.05 |

Figure 2:
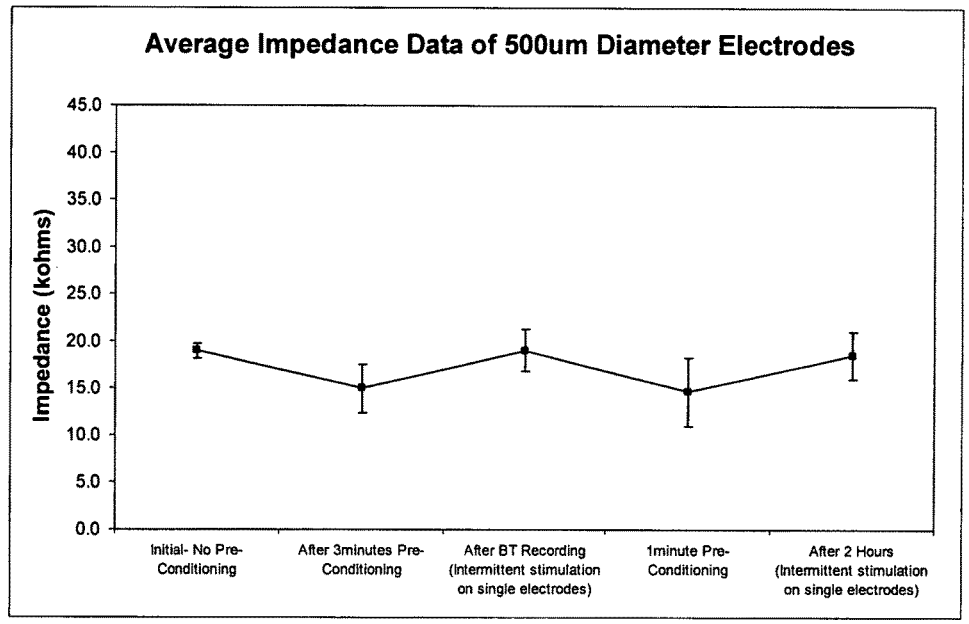
FIG. 2 shows a chart of average impedance data for 500 μm D electrodes.

FIGS. 1 and 2 are based on the measurements stated in previous tables 1-25 and show the advantageous effect of preconditioning of electrodes. The results can be summarized in the following table 26:

TABLE 26

| Diameter | Measurement | Initial - No Pre-Conditioning | After 3 minutes Pre-Conditioning | After Back Telemetry After 30 minutes | After Back Telemetry After 30 minutes 1 minute Pre-Conditioning | After 2 Hours (Intermittent stimulation on single electrodes) |
|---|---|---|---|---|---|---|
| 250 umD | Impedance (kohms) | 32.70 | 21.70 | 29.70 | 20.40 | 26.70 |
| | Standard deviation | 10.08 | 4.04 | 8.64 | 4.60 | 10.41 |
| 500 umD | Impedance (kohms) | 19.00 | 15.00 | 19.10 | 14.60 | 18.50 |
| | Standard deviation | 2.57 | 2.24 | 3.63 | 2.53 | 4.03 |

The table shows clearly that the preconditioning yields lower values for impedance (e.g. 32.70 v. 21.70 and 19.00 v. 15.00) and lower values for standard deviation (e.g. 10.08 v. 4.04 and 2.57 v. 2.24).

The pre-conditioning stimulation is performed on electrodes as for about 1 and about 3 minutes at 30-200 µA/30-120 Hz/0.1-0.1-0.1 ms-1.0-1.0-1.0 ms pulse width, preferred but not limited at about 100 µA/50 Hz/0.3-0.3-0.3 ms pulse width.

FIG. 1 shows results for 250 µm electrodes PCIT and FIG. 2 shows results for 500 µm electrodes PCIT. The charts show average values obtained from three patients (A, B, and C). Patient A obtained an array with 16 electrodes with 250 µm and patients B and C obtained an array with 8 electrodes with 250 µm and 8 electrodes with 500 µm diameters. The previous tables 1-25 show the measurements which lead to the average values summarized in table 26 and are shown in the charts in FIGS. 1 and 2.

Figure 3:
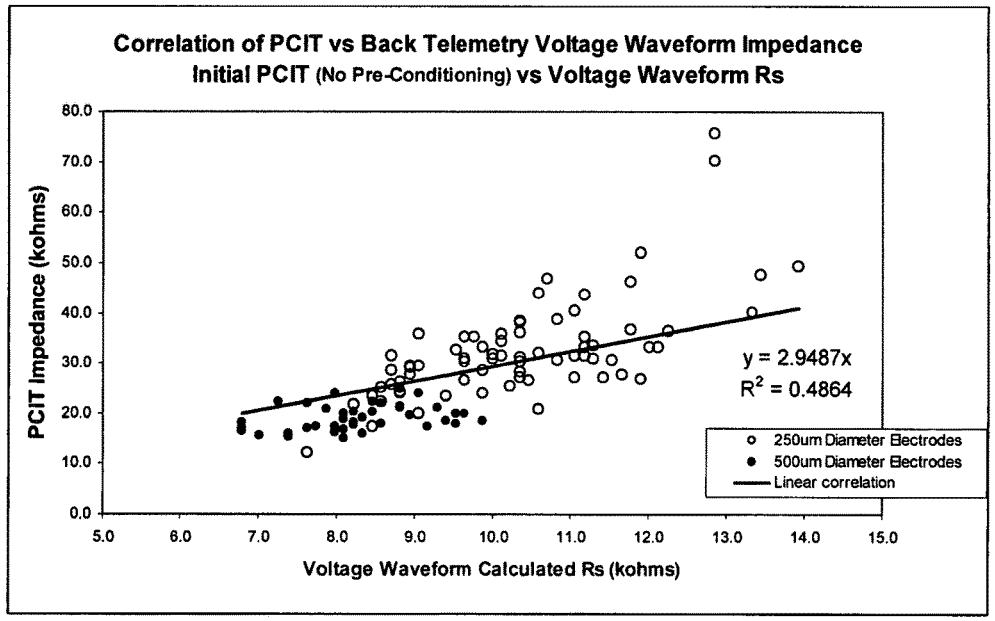
FIG. 3 shows a chart of correlation PCIT vs. back telemetry.
Figure 4:
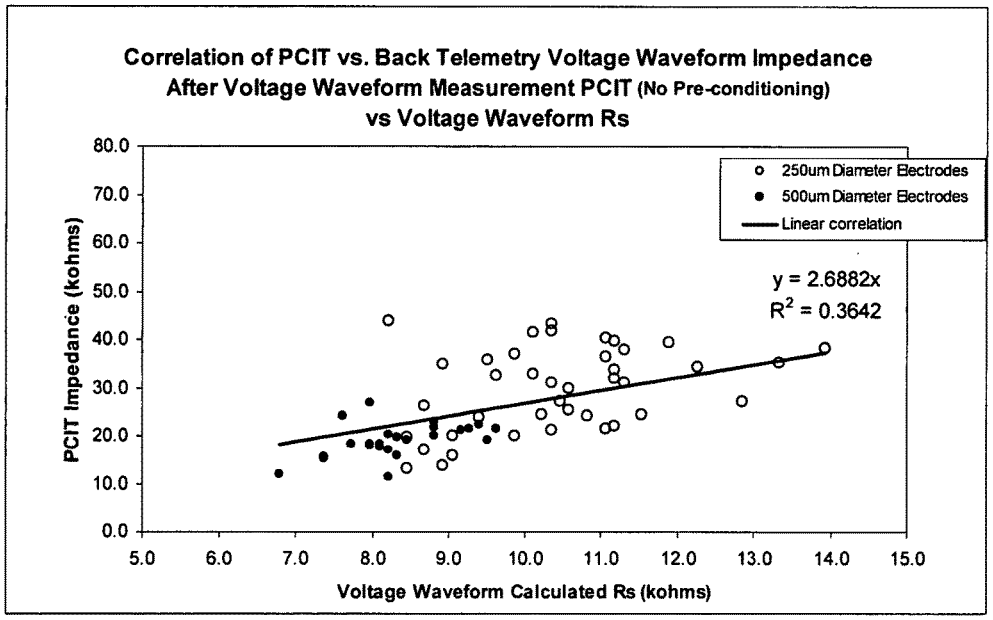
FIG. 4 shows a chart of correlation PCIT vs. back telemetry.
Figure 5:
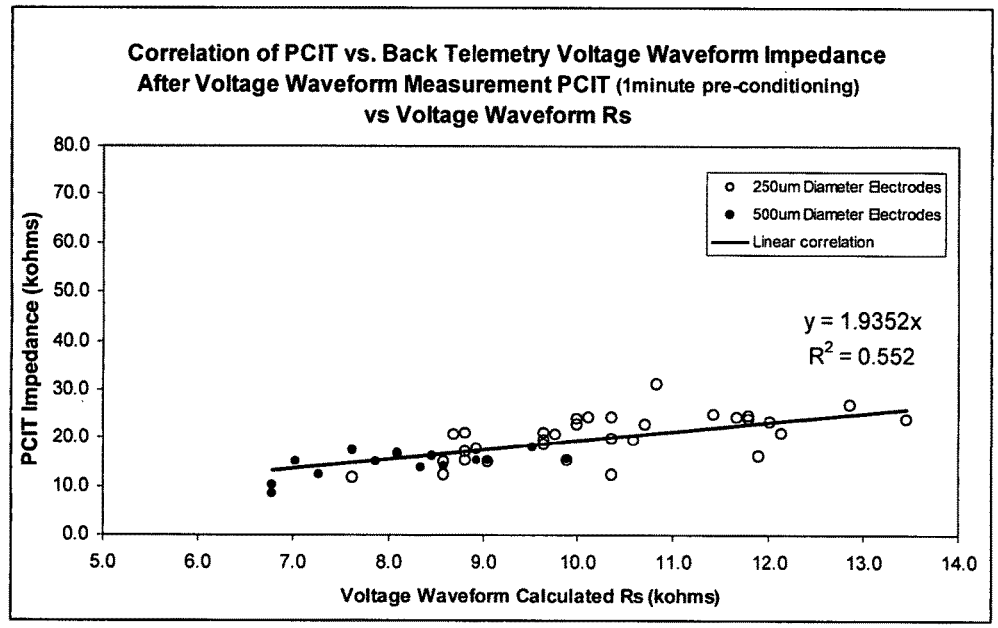
FIG. 5 shows a chart for 1 min. pre-conditioning PCIT vs. back telemetry.
Figure 6:
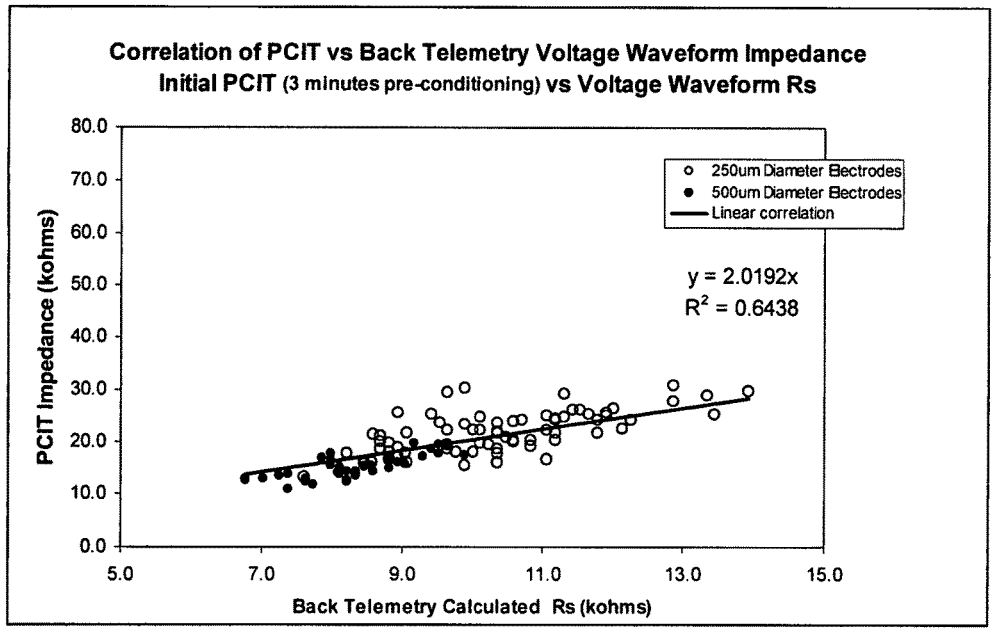
FIG. 6 shows a chart for 3 min. pre-conditioning PCIT vs. back telemetry.

FIGS. 3 to 6 show correlation of PCIT measurements and effects of pre-conditioning of electrodes. The charts in FIGS. 3-6 show an increase in improvement of the correlation. FIGS. 3 and 4 both show measurements without pre-conditioning. FIG. 3 shows correlation of PCIT vs. back telemetry voltage waveform impedance initial PCIT vs. voltage waveform Rs. FIG. 4 shows correlation of PCIT vs. back telemetry voltage waveform impedance after voltage waveform measurement PCIT vs. voltage waveform Rs. FIG. 5 shows correlation of PCIT vs. back telemetry voltage waveform impedance after voltage waveform measurement PCIT (1 minute pre-conditioning) vs. voltage waveform Rs. FIG. 6 shows correlation of PCIT vs. back telemetry voltage waveform impedance after voltage waveform measurement PCIT (3 minute pre-conditioning) vs. voltage waveform Rs. FIG. 6 shows the best correlation with 3 minutes of pre-conditioning.

Figure 7:
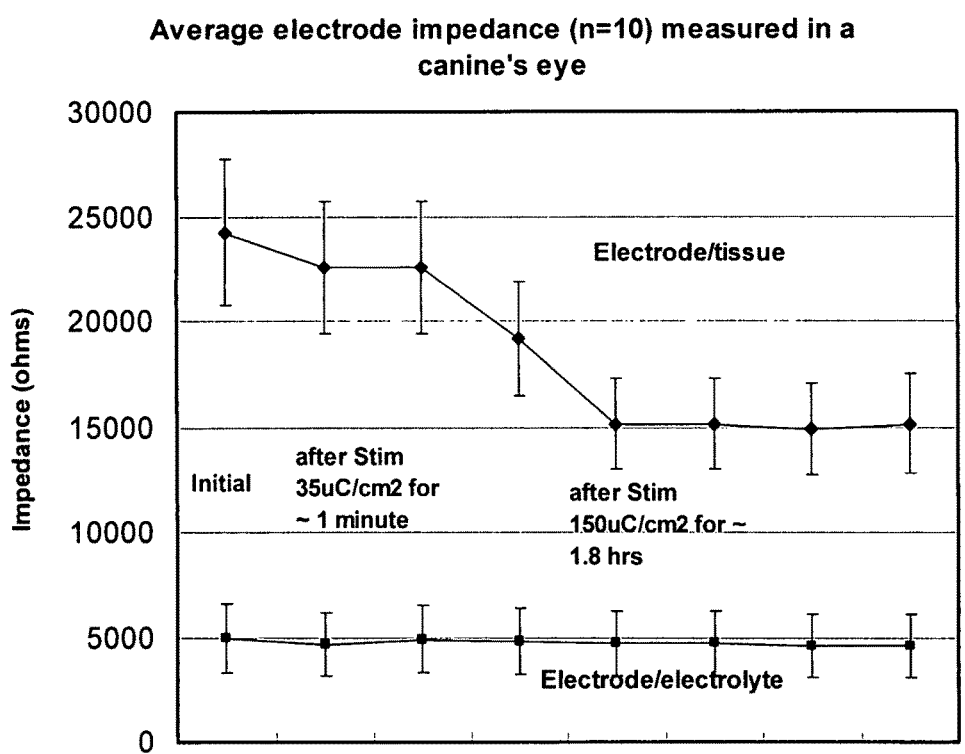
FIG. 7 shows a chart of average electrode impedance.

FIG. 7 shows an average electrode impedance (n=10) measured in a canine's eye. In-vivo electrode impedance changes measured in a canine's eye are shown therein. There were two groups of electrodes measured: one group with the electrodes in contact with retina tissue and the other with all the electrodes away from the tissue in saline. The impedance data from 10 electrodes for each group were averaged. The electrode/tissue impedance decreased dramatically upon electrical stimulation for the electrolyte in contact with the retina tissue while the electrode/electrolyte impedance had no significant changes for the electrodes being away from the tissue.

Accordingly, what has been shown is a method for measuring stable and reproducible electrode-tissue impedance, comprising preconditioning of an electrode-tissue interface. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A stimulation system for a visual prosthesis generating a stimulation signal to precondition an electrode-tissue interface, comprising:
   a computer;
   an implanted neural-stimulator, including a plurality of electrodes suitable to contact neural tissue;
   a video processing unit in communication with the computer and the implanted neural stimulator; and
   software, loaded in the computer, adapted to instruct the implanted neural stimulator through the video processing unit to deliver a first small electrical charge causing a non-faradaic reaction in the electrode tissue interface, including charge balanced biphasic square wave current pulses, for a predetermined duration of 1 second to 10 minutes, to deliver a second electrical charge within a predetermined delay of the predetermined duration and measure impedance after delivering the second electrical charge, and then to perform a stimulating method for a visual prosthesis having a plurality of electrodes.

2. The stimulation system for a visual prosthesis according to claim 1, configured to deliver the second electrical charge at similar electrode-tissue interface conditions to the first small electrical charge.

3. The stimulation system for a visual prosthesis according to claim 1 configured to deliver the first small electrical charge one electrode at a time or in groups of electrodes.

4. The stimulation system for a visual prosthesis according to claim 1 configured to deliver the first small electrical charge for all electrodes in an array of electrodes simultaneously.

5. The stimulation system for a visual prosthesis according to claim 4 configured to vary the first small electrical charge by pulse-width, amplitude and frequency.

6. The stimulation system for a visual prosthesis according to claim 1, configured to deliver the first small electrical charge at 10-300 µA at 15-120 Hz with 0.1-2.0 ms pulse width.

7. The stimulation system for a visual prosthesis according to claim 1, configured to deliver the first small electrical charge at 30-150 µA at 30-120 Hz with 0.2-1.0 ms pulse width.

8. The stimulation system for a visual prosthesis according to claim 1, configured to deliver the first small electrical charge at 80-120 µA at 40-60Hz with 0.4-0.6 ms pulse width.

* * * * *